United States Patent [19]
Drent

[11] Patent Number: 4,670,582
[45] Date of Patent: Jun. 2, 1987

[54] PROCESS FOR THE PREPARATION OF UNSATURATED CARBOXYLATE ESTERS

[75] Inventor: Eit Drent, Amsterdam, Netherlands

[73] Assignee: Shell Oil Company, Houston, Tex.

[21] Appl. No.: 896,681

[22] Filed: Aug. 15, 1986

[30] Foreign Application Priority Data

Sep. 27, 1985 [GB] United Kingdom ................ 8523859

[51] Int. Cl.$^4$ ............................................. C07C 51/14
[52] U.S. Cl. ............................. 560/233; 260/410.9 R; 558/353; 560/105; 560/114; 560/155; 560/201; 560/226
[58] Field of Search ............... 560/105, 114, 155, 204, 560/226, 233, 201; 558/353; 260/410.9 C

[56] References Cited

U.S. PATENT DOCUMENTS

| | | | |
|---|---|---|---|
| 3,349,119 | 10/1967 | Fenton | 560/233 |
| 3,437,676 | 4/1969 | Kutepow | 560/233 |
| 3,641,074 | 2/1972 | Fenton | 560/233 |
| 3,652,655 | 3/1972 | Fenton | 260/486 |
| 3,660,439 | 5/1972 | Schell | 560/233 |
| 4,414,409 | 11/1983 | Waller | 560/233 |

*Primary Examiner*—Michael L. Shippen

[57] ABSTRACT

Process for the preparation of carboxylate esters of alpha-ethylenically unsaturated alcohols by reacting an ethylenically unsaturated compound with carbon monoxide and an enolizable ketone in the presence of a catalytic system formed by combining a palladium catalyst, a triarylphosphine and a protonic acid having a $pK_a$ below 1.5, except hydrohalogenic acids and carboxylic acids.

21 Claims, No Drawings

PROCESS FOR THE PREPARATION OF UNSATURATED CARBOXYLATE ESTERS

FIELD OF THE INVENTION

The invention relates to a process for the preparation of carboxylate esters of alpha-ethylenically unsaturated alcohols.

BACKGROUND OF THE INVENTION

Carboxylate esters of alpha-ethylenically unsaturated alcohols can be polymerized to yield polyvinyl-type polymers. It has now been found that such carboxylate esters can be prepared with high selectivity and acceptable yield using relatively simple starting compounds.

SUMMARY OF THE INVENTION

The invention relates to a process for the preparation of carboxylate esters of alpha-ethylenically unsaturated alcohols, which process comprises causing an ethylenically unsaturated compound to react with carbon monoxide and an enolizable ketone in the presence of a catalytic system formed by combining:
(a) a palladium catalyst,
(b) a phosphine having the general formula (I)

in which $R^1$, $R^2$ and $R^3$ each individually represent an optionally substituted aryl group, and
(c) a protonic acid having a $pK_a$ below 1.5 as a promoter (measured at 18° C. in aqueous solution), except hydrohalogenic acids and carboxylic acids.

DESCRIPTION OF THE PREFERRED EMBODIMENTS

The reaction may schematically be represented by means of the following equation:

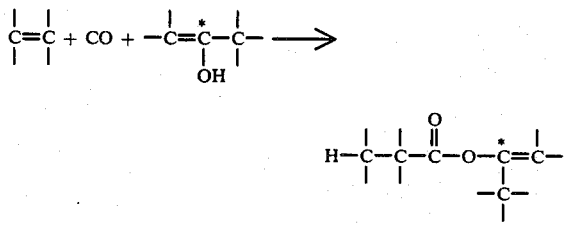

in which the hydroxy compound represents the anolized form of a ketone having the structure:

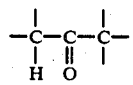

The two carbon atoms marked with an asterisk are the same carbon atoms.

The ethylenically unsaturated compound may be an optionally substituted alkene or an optionally substituted cycloalkene, preferably having in the range of from 2 to 30, in particular 2 to 20 and, more particularly, 2 to 10 carbon atoms per molecule, and preferably 1 to 3 carbon-carbon double bonds per molecule. Very good results have been obtained with ethylene. The alkene or cycloalkene may be substituted, for instance with one or more halogen atoms, or cyano, ester, alkoxy or aryl groups. Examples of suitable ethylenically unsaturated compounds are propene, 1-butene, 2-butene, isobutene, the isomeric pentenes, hexenes, heptenes, octenes and dodecenes, 1,5-cyclooctadiene, cyclododecene, 1,5,9-cyclododecatriene, methyl acrylate, ethyl acrylate, methyl methacrylate, acrylonitrile, acrylamide, N,N-dimethylacrylamide, vinyl chloride, allyl chloride, methyl allyl ether and styrene.

The enolizable ketone should have a hydrogen atom bound to a carbon atom adjacent to the carbonyl group. A wide variety of enolizable ketones may be used. The enolizable ketone may have optionally substituted alkyl, optionally substituted cycloalkyl or optionally substituted aryl groups bound to the carbonyl group. Preference is given to alkanones, two optionally substituted alkyl groups being bound to the carbonyl group. The optionally substituted alkanones suitably have in the range of from 3 to 30 carbon atoms per molecule. Particularly preferred are methyl alkyl ketones having in the range of from 3 to 30 carbon atoms per molecule, with the ketones having 3 or 4 carbon atoms per molecule preferred. Enolizable alkyl phenyl ketones are also very suitable, particularly those in which the alkyl group has in the range of from 1 to 10 carbon atoms. Very good results have been obtained with acetophenone. Other examples of suitable enolizable ketones are methyl butyl ketone, methyl isobutyl ketone, diheptyl ketone, dioctyl ketone, 3-butylheptyl ethyl ketone, methyl cyclohexyl ketone and ethyl phenyl ketone.

Enolizable ketones which are symmetric with respect to the carbonyl group yield one carboxylate ester. Enolizable ketones which are not symmetric with respect to the carbonyl group and in which ketones the two carbon atoms bound to the carbonyl group each carry a hydrogen atoms yield two different carboxylate esters of the same carboxylic acid, two different enolized forms being possible.

Both homogeneous and heterogeneous palladium catalysts may be used in the process according to the invention. Homogeneous catalyst are preferred. The palladium catalyst preferably contains a compound of divalent palladium. Suitable homogeneous catalysts are the salts of palladium with, for example, nitric acid, sulfuric acid or, particularly, alkanoic acids. Among the alkanoic acids, those having not more than 12 carbon atoms per molecule are preferred. Very good results have been obtained with palladium acetate. Moreover, palladium complexes may be used, for instance palladium acetylacetonate, tetrakistriphenylphosphine-palladium, bis-tri-o-tolylphosphinepalladium acetate or bis-triphenylphosphinepalladium sulfate. Palladium on charcoal and palladium bonded to an ion exchanger—for instance an ion exchanger comprising sulfonic acid groups—are examples of suitable heterogeneous catalysts.

It was found that when at least 5 mol of the phosphine having the general formula (I) are used per gram atom of palladium, a considerable increase in the reaction rate is obtained. Preferably, at least 20 mol of the phosphine having the general formula (I) are used per gram atom of palladium. In general, more than 500 mol phosphine per gram atom of palladium need not be used. Usually, in the range of from 10 to 150 mol phosphine per gram atom of palladium are used. If the palladium catalyst already contains phosphine, this should be taken into account when calculating the amount of phosphine to be used.

The protonic acid having a p$K_a$ below 1.5 preferably has a non-coordinating anion, by which is meant that little or no covalent interaction takes place between the palladium and the anion (cf. British Patent Application No. 2,058,074). Typical examples of such anions are $PF_6^-$, $SbF_6^-$, $BF_4^-$ and $ClO_4^-$. Preferred acids are sulfonic acids and acids that can be formed, possibly in situ, by interacting a Lewis acid such as, for example $BF_3$, $AsF_5$, $SbF_5$, $PF_5$, $TaF_5$ or $NbF_5$ with a Broensted acid such as, for example, a hydrogen halide, in particular HF, or fluorosulfonic acid, orthophosphoric acid or sulfuric acid. Specific examples of acids of the latter type are fuorosilicic acid, $HBF_4$, $HPF_6$ and $HSbF_6$. Examples of suitable sulfonic acids are fluorosulfonic acid, chlorosulfonic acid and the hereinafter specified sulfonic acids.

A preferred group of non-carboxylic protonic acids having a p$K_a$ below 1.5 are those having the general formula (II):

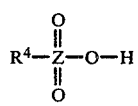

(II)

wherein Z represents sulfur or chlorine and, if Z is chlorine, $R^4$ represents oxygen and, if Z is sulfur, $R^4$ represents an OH group or an optionally substituted hydrocarbon group.

When the hereinbefore-stated acids of the general formula (II) are used in the process according to the invention, the anions thereof can be considered to be non-coordinating.

The optionally substituted hydrocarbon group represented by $R^4$ is preferably an alkyl, aryl, aralkyl or alkaryl group having 1 to 30, in particular 1 to 14, carbon atoms. The hydrocarbon group may be substituted for example with halogen atoms, in particular fluorine atoms. Examples of suitable acids of the general formula (II) are perchloric acid, sulfuric acid, 2-hydroxypropane-2-sulfonic acid, benzenesulfonic acid, 1-naphthalenesulfonic acid, 2-naphthalenesulfonic acid, p-toluenesulfonic acid and trifluoromethanesulfonic acid, with p-toluenesulfonic acid being the most preferred.

The optionally substituted aryl groups $R^1$, $R^2$ and $R^3$ in the general formula (I) preferably contain not more than 18, and in particular in the range of from 6 to 14 carbon atoms. Examples of suitable aryl groups are naphthyl groups and, in particular, phenyl groups. Suitable substituents on the aryl groups are halogen atoms and alkyl, aryl, alkoxy, trihalomethyl, cyano, dialkylamino and alkanoyloxy groups. Examples of suitable phosphines are tri(p-tolyl)phosphine, tri(p-methoxyphenyl)phosphine and, in particular, triphenylphosphine.

The number of equivalents of the phosphine having the general formula (I) which is used per equivalent of non-carboxylic protonic acid having a p$K_a$ below 1.5 is not critical and may vary within wide limits. This number is suitably in the range of from 0.5 to 50. The quantity of palladium catalyst is not critical and may vary within wide limits. Preference is given to the use of quantities in the range between $10^{-5}$ and $10^{-1}$ gram atom palladium per mol of ethylenically unsaturated compound.

A separate solvent is not essential in the process according to the invention, and often a large excess of one of the reactants, usually the enolizable ketone, may form a convenient liquid phase. However, it may in some cases be desirable to use a separate solvent and any inert solvent may be used. A suitable solvent may for example, be selected from aromatic hydrocarbons, for example benzene, toluene, ethylbenzene and the three xylenes; sulfoxides, for example dimethyl sulfoxide and diethyl sulfoxide; sulfones, for example diisopropyl sulfone and tetrahydrothiophene 1,1-dioxide (also referred to as "sulfolane") and ethers, for example anisole, 2,5,8-trioxanonane (also referred to as "diglyme"), diphenyl ether and diisopropyl ether.

In the process according to the invention the carbon monoxide may be used pure or diluted with an inert gas, such as nitrogen, noble gases or carbon dioxide. Generally, the presence of more than 10% by volume of hydrogen is undesirable, since under the reaction conditions it may cause hydrogenation of carbon-carbon double bonds. Preference is given to the use of pure carbon monoxide or a carbon monoxide-containing gas which contains less than 5% by volume of hydrogen.

The process according to the invention permits the use of very mild reaction conditions. Temperatures in the range of from 50° C. to 200° C., especially 100° C. to 150° C., are generally suitable. The pressure may vary over a wide range. Generally, a pressure in the range from 1 to 100 bar is suitable, with pressures of from 5 to 50 bar being preferred. Pressures higher than 100 bar may be used, but are usually economically unattractive.

The molar ratio of the ethylenically unsaturated compound to the enolizable ketone is not critical and may vary within wide limits. The molar ratio carbon-carbon double bonds to enolizable ketone may lie, for instance, between 0.1:1 and 10:1.

The process according to the invention may be carried out batchwise, continuously or semi-continuously.

The following examples are intended to illustrate the invention and are not to be construed as limiting the invention. The selectivity to a certain compound, expressed in a percentage, is defined as 100 a/b, in which "a" is the amount of ketone that has been converted into that certain compound and "b" is the total amount of ketone that has been converted.

EXAMPLE 1

A 250-ml magnetically stirred Hastelloy C autoclave ("Hastelloy" is a trade name) was charged with o-xylene (50 ml), methyl ethyl ketone (20 ml), palladium acetate (0.2 mmol), triphenylphosphine (10 mmol) and p-toluenesulfonic acid (2 mmol). The autoclave was flushed with carbon monoxide, filled with carbon monoxide and ethylene until partial pressures thereof of 20 bar each were obtained and heated to a temperature of 110° C. After a reaction time of 5 h at this temperature the contents of the autoclave were analyzed by means of gas-liquid chromatography. The conversion of methyl ethyl ketone was 30%, with a total selectivity to 1-ethylvinyl propionate and 1-methylallyl propionate of 95%; the former and the latter propionate were obtained in a molar ratio of 2.3.

EXAMPLE 2

The procedure of Example 1 was repeated with the difference that 20 ml of methyl ethyl ketone were replaced with 20 ml of acetone. The conversion of acetone was 26%, with a selectivity to isopropenyl propionate of 95%.

EXAMPLE 3

The procedure of Example 1 was repeated with the difference that 20 ml of methyl ethyl ketone were replaced with 20 ml of acetophenone. The conversion of acetophenone was 15%, with a selectivity to 1-phenylvinyl propionate of 95%.

EXAMPLE 4

An experiment was carried out in the manner of Example 1, using o-xylene (50 ml), acetophenone (20 ml), palladium acetate (0.2 mmol), triphenylphosphine (20 mmol) and p-toluenesulfonic acid (5 mmol). After a reaction time of 2.5 h at 100° C. the conversion of acetophenone was 15%, with a selectivity to 1-phenylvinyl propionate of 95%.

EXAMPLE 5

The procedure of Example 4 was repeated with the difference that 10 mmol instead of 5 mmol of p-toluenesulfonic acid were used and that the reaction was carried out for 3.5 h at 115° C. The conversion of acetophenone was 23%, with a selectivity to 1-phenylvinyl propionate of 95%.

EXAMPLE 6

An experiment was carried out in the manner of Example 1, using o-xylene (50 ml), acetophenone (20 ml), palladium acetate (0.2 mmol), triphenylphosphine (30 mmol) and p-toluenesulfonic acid (10 mmol). The partial pressures of ethylene and carbon monoxide were 30 bar each. After a reaction time of 5 h at 125° C. the conversion of acetophenone was 30%, with a selectivity to 1-phenylvinyl propionate of 95%.

EXAMPLE 7

An experiment was carried out in the manner of Example 1, using o-xylene (50 ml), acetophenone (20 ml), palladium acetate (0.1 mmol), triphenylphosphine (50 mmol) and p-toluenesulfonic acid (15 mmol). The partial pressures of ethylene and carbon monoxide were 30 bar each. After a reaction time of 5 h at 125° C. the conversion of acetophenone was 33%, with a selectivity of 1-phenylvinyl propionate of 95%.

EXAMPLE 8

An experiment was carried out in the manner of Example 1, using o-xylene (50 ml), acetophenone (20 ml), palladium acetate (0.1 mmol), triphenylphosphine (30 mmol), p-toluenesulfonic acid (10 mmol) and propionic acid (2 ml). The partial pressures of ethylene and carbon monoxide were 30 bar each. After a reaction time of 5 h at 125° C. the conversion of acetophenone was 25%, with a selectivity to 1-phenylvinyl propionate of 95%. Propionic acid was converted into propionic anhydride with a yield of 90%.

EXAMPLE 9

An experiment was carried out in the manner of Example 1, using o-xylene (50 ml), acetophenone (20 ml), palladium acetate (0.1 mmol), triphenylphosphine (50 mmol) and methanesulfonic acid (15 mmol). The partial pressures of ethylene and carbon monoxide were 30 bar each. After a reaction time of 5 h at 125° C. the conversion of acetophenone was 22%, with a selectivity to 1-phenylvinyl propionate of 95%.

EXAMPLE 10

The procedure of Example 9 was repeated with the difference that 15 mmol of methanesulfonic acid were replaced with 15 mmol of mesitylenesulfonic acid. The conversion of acetophenone was 14%, with a selectivity to 1-phenylvinyl propionate of 95%.

EXAMPLE 11

An experiment was carried out in the manner of Example 1, using diglyme (50 ml), acetophenone (20 ml), palladium acetate (0.1 mmol), triphenylphosphine (50 mmol) and p-toluenesulfonic acid (15 mmol). The partial pressures of ethylene and carbon monoxide were 30 bar each. After a reaction time of 5 h at 125° C. the conversion of acetophenone was 30%, with a selectivity to 1-phenylvinyl propionate of more than 95%.

EXAMPLE 12

An experiment was carried out in the manner of Example 1, using diglyme (50 ml), acetophenone (20 ml), palladium acetate (0.1 mmol), tri(m-chlorophenyl)phosphine (20 mmol) and p-toluenesulfonic acid (5 mmol). The partial pressures of ethylene and carbon monoxide were 30 bar each. After a reaction time of 3 h at 125° C. the conversion of acetophenone was 8%, with a selectivity to 1-phenylvinyl propionate of more than 95%.

EXAMPLE 13

The procedure of Example 11 was repeated with the difference that the partial pressures of ethylene and carbon monoxide were 20 and 40 bar, respectively. The conversion of acetophenone was 25%, with a selectivity to 1-phenylvinyl propionate of 95%.

EXAMPLE 14

The procedure of Example 11 was repeated with the difference that the partial pressures of ethylene and carbon monoxide were 40 and 20 bar, respectively. The conversion of acetophenone was 25%, with a selectivity to 1-phenylvinyl propionate of 95%.

EXAMPLE 15

The procedure of Example 11 was repeated with the difference that 50 ml instead of 20 ml of acetophenone were used and that no diglyme was present. The conversion of acetophenone was 18%, with a selectivity to 1-phenylvinyl propionate of 95%.

COMPARATIVE EXPERIMENT A

The procedure described in Example 1 was repeated with the difference that p-toluenesulfonic acid (2 mmol) was replaced with benzenephosphonic acid ($pK_a = 1.5$, 2 mmol). The conversion of the ketone was below 5% and propionate could not be detected in the reaction mixture.

COMPARATIVE EXPERIMENT B

The procedure described in Example 1 was repeated with the difference that p-toluenesulfonic acid (2 mmol) was replaced with 2,6-dichlorobenzoic acid ($pK_a = 1.5$, 2 mmol). The conversion of ketone was below 5% and propionate could not be detected in the reaction mixture.

I claim as my invention:

1. A process for the preparation of carboxylate esters of alphaethylenically unsaturated alcohols, which process comprises reacting an ethylenically unsaturated compound with carbon monoxide and an enolizable ketone in the presence of a catalytic system formed by combining:
   (a) a palladium catalyst,
   (b) a phosphine having the general formula (I)

in which $R^1$, $R^2$ and $R^3$ each individually represent an optionally substituted aryl group, and
   (c) a protonic acid having a $pK_a$ below 1.5 as a promoter (measured at 18° C. in aqueous solution), except hydrohalogenic acids and carboxylic acids.

2. The process of claim 1 wherein the ethylenically unsaturated compound is an optionally substituted alkene having in the range of from 2 to 30 carbon atoms per molecule.

3. The process of claim 2 wherein the optionally substituted alkene has in the range of from 2 to 10 carbon atoms per molecule.

4. The process of claim 3 wherein the alkene is ethylene.

5. The process of claim 1 wherein an optionally substituted alkanone having in the range of from 3 to 30 carbon atoms per molecule is used as enolizable ketone.

6. The process of claim 5 wherein the alkanone is a methyl alkyl ketone.

7. The process of claim 5 wherein the alkanone has 3 to 4 carbon atoms per molecule.

8. The process of claim 1 wherein an enolizable alkyl phenyl ketone is used.

9. The process of claim 8 wherein the enolizable ketone is acetophenone.

10. The process of claim 1 wherein the palladium catalyst contains a compound of divalent palladium.

11. The process of claim 10 wherein the compound of divalent palladium is a palladium alkanoate.

12. The process of claim 11 wherein the palladium alkanoate is palladium acetate.

13. The process of claim 1 wherein at least 5 mol of the phosphine having the general formula (I) are used per gram atom of palladium.

14. The process of claim 1 wherein an acid with a non-coordinating anion is used as promoter.

15. The process of claim 14 wherein a sulfonic acid or an acid that can be formed by interaction of a Lewis acid with a Broensted acid is used as promoter.

16. The process of claim 1 wherein an acid having the general formula (II)

in which Z represents a sulphur or a chlorine atom, and, if Z represents a chlorine atom, $R^4$ represents an oxygen atom, and, if Z represents a sulfur atom, $R^4$ represents an OH group or an optionally substituted hydrocarbyl group, is used as a promoter.

17. The process of claim 16 wherein the hydrocarbyl group represented by $R^4$ is an alkyl, aryl, aralkyl or alkaryl group having not more than 30 carbon atoms.

18. The process of claim 16 wherein the acid is p-toluenesulfonic acid.

19. The process of claim 1 wherein the aryl groups represented by the groups $R^1$, $R^2$ and $R^3$ in formula (I) have in the range of from 6 to 14 carbon atoms.

20. The process of claim 19 wherein the aryl groups represented by the groups $R^1$, $R^2$ and $R^3$ are phenyl groups.

21. The process of claim 1 wherein said process is carried out at a temperature in the range of from 50° C. to 200° C.

* * * * *